United States Patent [19]
Van de Velde

[11] Patent Number: 5,543,866
[45] Date of Patent: Aug. 6, 1996

[54] SCANNING LASER OPHTHALMOSCOPE FOR BINOCULAR IMAGING AND FUNCTIONAL TESTING

[75] Inventor: Frans J. Van de Velde, Boston, Mass.

[73] Assignee: Jozef F. Van de Velde, Oosterzele, Belgium

[21] Appl. No.: 178,777

[22] Filed: Jan. 7, 1994

[51] Int. Cl.$^6$ ........................................... A61B 3/10
[52] U.S. Cl. ........................ 351/221; 351/205; 351/211
[58] Field of Search ................................ 351/205, 206, 351/204, 209, 210, 211, 221; 359/201, 202, 216, 226

[56] References Cited

U.S. PATENT DOCUMENTS

| | | |
|---|---|---|
| 4,213,678 | 7/1980 | Pomerantzeff et al. . |
| 4,712,895 | 12/1987 | Kamiyama et al. ............ 351/204 |
| 5,152,295 | 10/1992 | Kobayashi et al. ............ 351/221 |

OTHER PUBLICATIONS

Nasemann and Burk, Scanning laser ophthalmoscopy . . . ISBN 3-928036-01-7 Chapter 1 and 2, pp. 23 to 46.
Van de Velde et al. Microperimetry with the SLO in Perimetry Update, ISBN 09-6299-075-4, pp. 94 to 101.

Primary Examiner—William L. Sikes
Assistant Examiner—Hung Xuan Dang

[57] ABSTRACT

A binocular scanning laser ophthalmoscope expands the range of clinical applications of the conventional scanning laser ophthalmoscope, being able of presenting the scanning laser raster with or without graphics to one eye or to both at the same time and simultaneously allowing the observation of either eye or both on the display monitor. The device, including a beamsplitter, mirrors, and optical filters, enables switching up to video between the different options without the need for moving the scanning laser ophthalmoscope from one eye to the other. Lenses can be inserted in the optical pathway for the correction of ametropia. A pupillary distance control for both eyes optimizes the Maxwellian view on both sides.

10 Claims, 2 Drawing Sheets

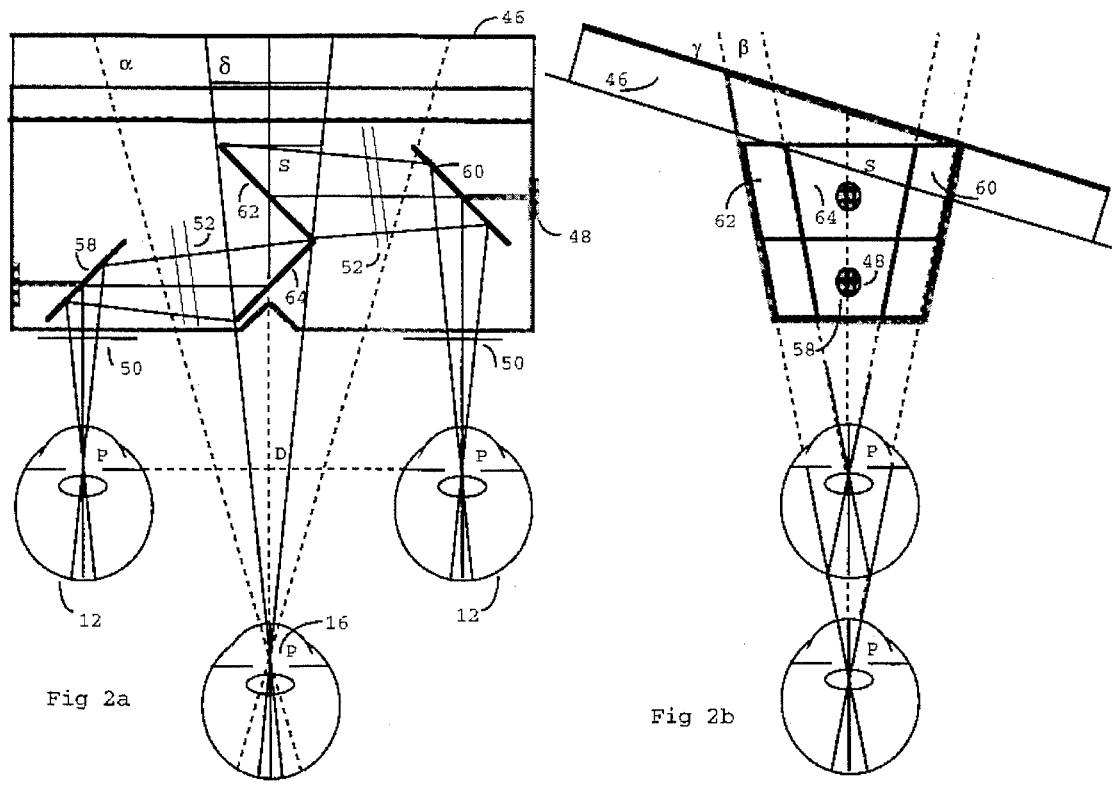
Fig 2a
Fig 2b
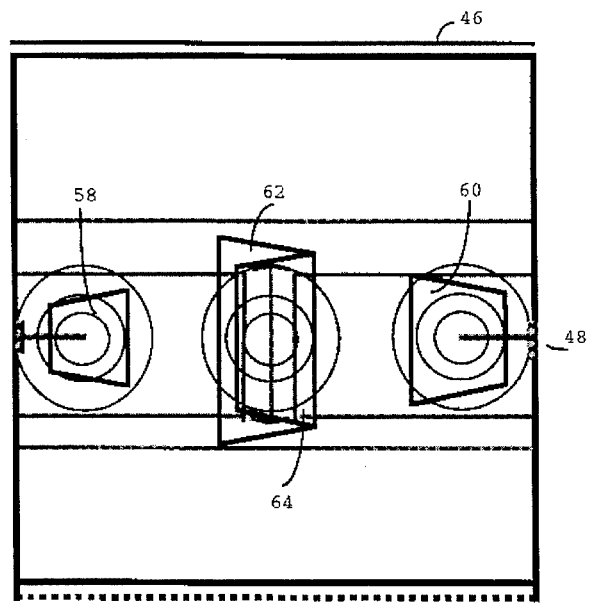
Fig 2c

SCANNING LASER OPHTHALMOSCOPE FOR BINOCULAR IMAGING AND FUNCTIONAL TESTING

BACKGROUND-FIELD OF INVENTION

This invention relates generally to instruments for examining the eye and in particular to an electro-optical ophthalmoscope with a modified and extended optical pathway. It specifically provides a precise binocular visual representative of the eye fundus and eye functioning on a display monitor.

BACKGROUND-DESCRIPTION OF PRIOR ART

The ophthalmoscope is well known as an important aid for studying and examining the eye, and in particular, the fundus of the eye. As a result of great interest in preserving man's eyesight, ophthalmoscopes of various constructions have been built and used. The latest version of the ophthalmoscope, a scanning laser ophthalmoscope, is particularly appealing because of its unique capability of combining the visualization of the retina or eye fundus with certain psychophysical and electrophysiological testing procedures. These testing procedures are a well known aid in studying the subjective or objective functioning of the visual pathways, from the retina to the brain cortex. Many different stimuli that are used in visual psychophysics, for example a Snellen E acuity letter or small fixation cross, can be projected onto the fundus with the help of the scanning laser ophthalmoscope. Overlay graphics are then used to display the stimulus on the fundus image in real-time. Detailed functional mapping of the fundus is thereby possible. Such functional mapping could be the outline of the retinal area used for fixating a small cross.

However, until the invention, all projecting ophthalmoscopes, including the scanning laser ophthalmoscope, have been limited to the examination of one eye at a time, excluding binocular imaging and presentation of stimuli or graphics, psychophysical stimuli in particular, to both eyes simultaneously. Binocular imaging of the subject's eyes with the instrument should not be confused with traditional binocular and stereoscopic observation of one eye fundus with the well known binocular indirect ophthalmoscope.

Furthermore, established classic tests for binocular vision, such as the cover-uncover, Maddox, Bagolini, Worth, and synoptophore do not even attempt to determine the position of the stimulus on the retina.

It is possible to perform video angiographies using fluorescein or indocyanin green with the scanning laser ophthalmoscope. No single ophthalmoscope has been capable so far of recording the dye transit in both eyes at the same time. Repeat injections of the dye are necessary to compare important phases of the dye transit in either retina. This results in a waste of material, time, discomfort for the subject and an increased risk for medical complications.

OBJECTS AND ADVANTAGES

The principal objects of this invention are therefore to provide a binocular scanning laser ophthalmoscope having the capability of presenting stimuli or graphics to one or both eyes simultaneously and to visualize on the display monitor either fundus; the separation in time between the display of either eye can be as small as the time to display one video field and without the need for moving the subject and binocular scanning laser ophthalmoscope relative to each other. Several diverse objects and advantages of the device can be envisioned. In imaging, bilateral simultaneous recording of fluorescein angiographies at the optic disc can be useful to calculate the relative differences between right and left arm-brain circulation times (carotids). By displaying both fundi simultaneously, a complete dye transit can be obtained with a single injection for the two eyes, specifically detailing the fast early phases of the transit. Prism or angular deviations can be precisely measured in strabology, diplopia, microstrabismus, anomalous correspondence by using the fundus landmarks as fiducial coordinates during binocular graphics presentation. The use of infra-red light and animated graphics are important advantages in pediatric ophthalmology when implementing the cover-uncover, Madox, and Bagolini tests.

Summation effects of bilateral pattern visual evoked responses can be documented in clinical electrophysiology.

It is an accepted fact that when both eyes can send similar information to the brain, the binocular performance of vision is as a rule superior to that of the monocular components alone. This summation activity at the brain level is evident for a number of psychophysical tasks including fixation, acuity, reading, contrast sensitivity, and the measurement of visual evoked responses. On the contrary, disparity of input to the brain often leads to binocular suppression of the weaker eye, and decreased monocular performance of the better eye as well. This is typically observed in certain forms of strabismus, anisometropia, central scotomas, and related conditions. It has been demonstrated that the two phenomena of suppression and synergism described above are relevant to visual functioning when macular disease, in particular age related macular degeneration, is present. Knowledge of binocular fixation, acuities, and reading performance may lead to insight in physiopathology, improved laser treatment, and low vision strategies for age related macular degeneration, the leading cause of legal blindness in the United States. For example, conjugate, similar scars in both eyes can be caused by the disease or laser treatment. These scars will reduce the binocular field of view for the subject but can also lead to synergism of potentially corresponding preferred retinal fixation loci in both eyes.

Further objects and advantages of my invention will become apparent from a consideration of the drawings and ensuing description.

DESCRIPTION OF THE DRAWINGS

Features and advantages of the invention will appear from the following description of preferred embodiments of the invention, taken together with the drawings in which:

FIG. 2a, 2b, 2c are engineering views showing frontal, lateral and superior projections of the device. An engineering view is used because the dimensions of the optical path, and the spatial relationship between subject and binocular scanning laser ophthalmoscope are critical in the construction of the instrument.

REFERENCE NUMERALS IN DRAWINGS

Figure 1:
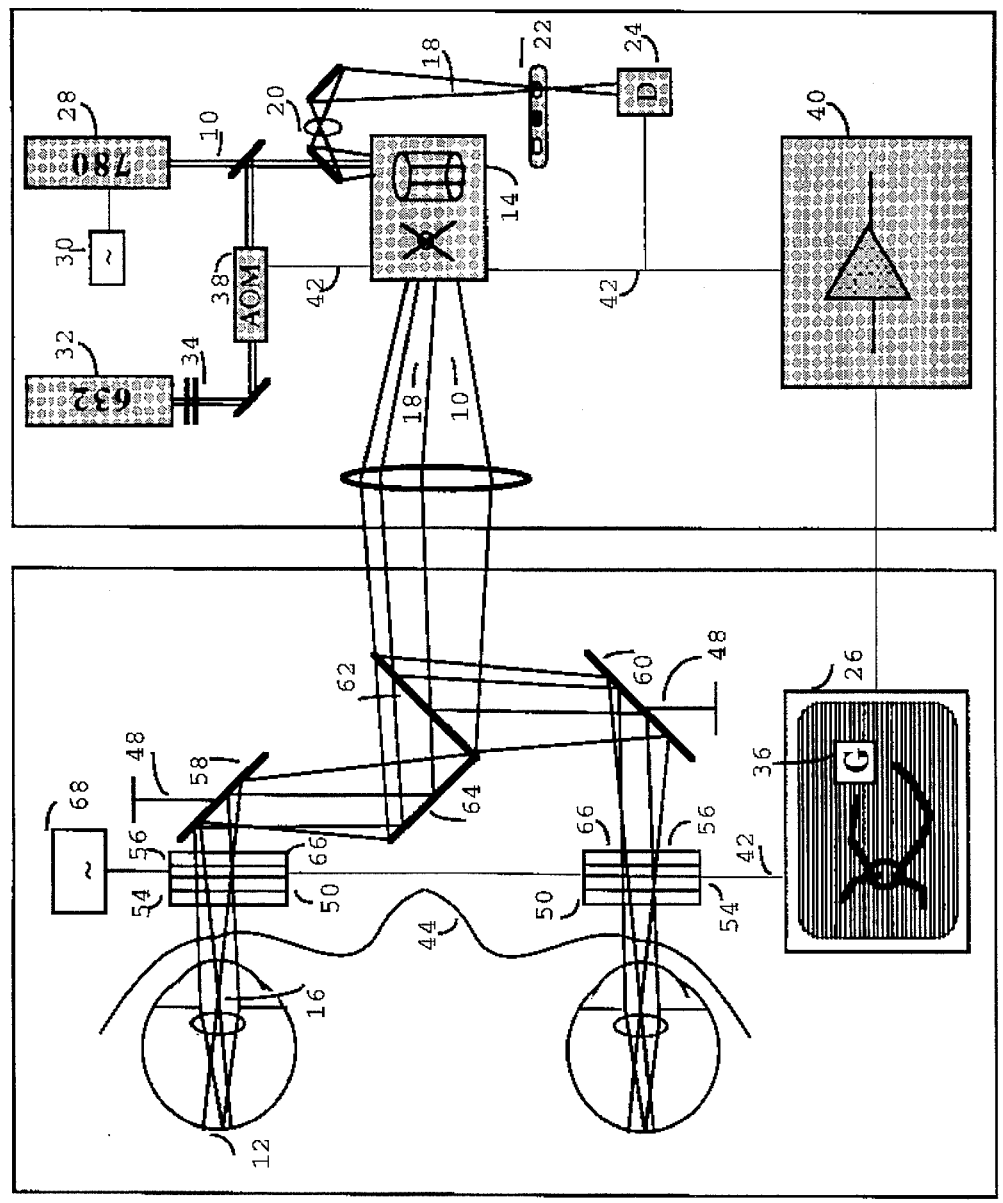
FIG. 1 is a diagrammatic representation, illustrating the general mode of operation of the binocular scanning laser ophthalmoscope.

10 Prefocussed narrow Gaussian beam of laser light

12 Posterior pole of the eye, fundus or retina with scanning laser raster and graphics

14 Scanners, including polygon and galvanometer

16 Maxwellian view of the illuminating path
18 Reflected and backscattered light from the eye
20 Beam separator
22 Pinhole at the retinal conjugate plane
24 Avalanche photodiode
26 Video display monitor
28 Diode infra-red 780 nm laser
30 Amplitude modulation of diode laser
32 He-Ne red 632 nm laser
34 Pair of adjustable linear polarizers
36 Graphics on the retina, visible as overlays
38 Acousto-optic modulator
40 Electronic circuitry of scanning laser ophthalmoscope
42 Distribution of common synchronization to different components
44 Nose, cheeks and eyebrows
46 Scanning laser ophthalmoscope window or key reference plane
48 Bilateral screw adjustment of pupillary distance PD
50 Slots that contain filters, lenses and liquid crystal switches
52 Additional angulated slots
54 Filters comprising neutral density, polarizing, bandpass
56 Lenses comprising spherical, cylindrical and prismatic
58 Flat mirror 1
60 Flat mirror 2
62 Beamsplitter
64 Flat mirror 3
66 Optical components
68 Electronic circuitry for switching liquid crystal shutters

DESCRIPTION AND OPERATION OF AN EMBODIMENT-FIG. 1, 2a, 2b, 2c

A typical embodiment of the binocular scanning laser ophthalmoscope is illustrated by FIG. 1 and 2a, 2b, 2c. The principles of scanning laser ophthalmoscopy are described in detail in the prior art. Features relevant to the invention are further discussed.

THE SCANNING LASER OPHTHALMOSCOPE PROPER

A prefocussed narrow Gaussian beam of laser light 10, typically 12 μ in diameter at the retinal plane, is scanned over the posterior pole of the eye 12 in a sawtooth manner with the help of scanning mirrors, currently a polygon and galvanometer 14. Both fast horizontal 15 KHz and slower vertical 60 Hz deflections of the flying laser spot are at standard video RS-170 rates with blanking intervals and create the rectangular laser beam raster that is seen by the subject. A Maxwellian view 16 is used in the illuminating portion of the scanning laser ophthalmoscope: the pivot point of the scanning laser beam is actually a tiny three dimensional volume situated in the iris plane with an average waist of less than 1 mm. Typically a rectangular area of approximately 0.5 $cm^2$ on the retina is illuminated. This corresponds to a field of view of 40 degrees in diagonal or 32.7 degrees horizontally by 23.4 degrees vertically. The field of view can be changed with electronic or optical adjustments of the optical path. It is important to understand that the subject will not see a flying spot but rather a rectangle filled with thin horizontal stripes because of the temporal summation characteristics of the visual system. The reflected and backscattered light from the eye 18, now filling the pupil, is descanned over the same mirrors, separated 20 from the illuminating beam and passed through a pinhole 22 at the retinal conjugate plane before reaching a fast and sensitive avalanche photodiode 24. This confocal detection method is essential for obtaining high contrast pictures of the retina with infra-red illumination by eliminating stray light at the pinhole. The amount of light on the photodetector is translated into a voltage that modulates the intensity of an electron beam on the visual display cathode ray tube monitor 26. The electron beam moves synchronically with the scanning laser beam and a real-time video image of the fundus is likewise created on the display monitor. Two lasers sources are aligned to illuminate the retina. The two lasers serve a different purpose. A high intensity diode infra-red 780 nm laser 28, electrically modulated 30 and vertically polarized, is nearly invisible to the subject. It produces the retinal image on the display monitor. A superimposed low intensity He-Ne red 632.8 nm red laser 32, modulated with a pair of adjustable linear polarizers 34 and horizontally polarized, is visible to the eye. It is used to draw psychophysical stimuli 36 in the laser raster for projection onto the retina. These stimuli are created by amplitude modulation of the laserbeam at video rates as the red light transverses an acousto-optic modulator 38. The acousto-optic modulator is driven by a standard video source that contains the graphics information and is genlocked to the crystal clock of the electronic circuitry 40. Master timing signals are derived from the spinning polygon. It is important to understand the reasons for using two different lasers. The scanning laser ophthalmoscope is very light efficient: about three orders of magnitude less light is necessary to visualize the fundus when compared with conventional ophthalmoscopes. However this light is still orders of magnitude the amount used for typical psychophysical testing. The problem is solved by using a 780 nm laser with sufficiently high output and for which the silicon detector of the scanning laser ophthalmoscope, but not the eye, is most sensitive, in combination with a low power 632 nm laser, for which the human eye is sensitive but insufficient for visualizing the fundus. This explains also why the stimuli which are perceived by the subject are usually not visible in the retinal picture, unless very bright. The exact position and characteristics of the stimuli can however be shown in real-time on the retinal image with the help of overlays as all image video out of the scanning laser ophthalmoscope, scanners, and graphics video into the acousto-optic modulator are synchronized to the same crystal clock 42. Two laser sources also allow binocular presentation of graphics and independent viewing of either retina as further explained.

The scanning laser ophthalmoscope preferably uses achromatic refracting surfaces, such as mirrors and a polygon instead of lenses and acousto-optic deflectors, to prevent chromatic aberrations when combining two different wavelengths.

OTHER LASERSOURCES FOR THE SCANNING LASER OPHTHALMOSCOPE

In fluorescein angiography with the scanning laser ophthalmoscope, a 632 nm He-Ne laser is usually combined with a 488 nm laser that replaces the functions of the 780 nm laser described above. The 488 nm argon laser is used for excitation of the fluorescein molecules. A 500 nm barrier filter with no pinhole at the retinal conjugate plane is used to separate the backscattered excitation light from the fluorescent light. In indocyanin green angiography with the scanning laser ophthalmoscope, a 780 nm diode laser is kept for excitation of the indocyanin green molecules. A 800 nm barrier filter with no pinhole at the retinal conjugate plane is then used to separate the backscattered light from the fluorescent light.

The diode 780 nm laser can be replaced by a diode laser of longer wavelength, for example 904 nm. For every 10 nm increase in wavelength of the diode laser beyond 670 nm, the efficiency for stimulating the retina under photopic testing conditions will be reduced to one half. This is useful in making the infra-red background illumination for visualizing the retina on the display monitor even less visible to the subject. Surface-emitting quantum-well laser diodes are of increasing interest, and offer the advantages of high packing densities on a wafer scale. An array of up to a million tiny individually modulated cylindrical $In_{0.2}Ga_{0.8}As$ surface-emitting quantum-well laser diodes with lasing wavelengths in the vicinity of 970 nm and shorter can substitute the traditional laser sources and scanners of a scanning laser ophthalmoscope. This will render the device more compact, less noisy, and less susceptible to mechanical wear and tear.

EXTERNAL APPEARANCE OF THE BINOCULAR SCANNING LASER OPHTHALMOSCOPE

Measurements given are for use with the Rodenstock Scanning Laser Ophthalmoscope 101 or 102 (Munich, Germany). These measurements are readily adapted for other embodiments of the scanning laser ophthalmoscope by s/he who is skilled in the art.

The principal modifications of the optical components of the binocular scanning laser ophthalmoscope are contained in a moulded closed encasement for dust protection and painted matt black on the inside to minimize unwanted scatter. It provides as much sparing as possible for the bodily parts such as the nose, cheeks and eyebrows 44 and has one posterior and two anterior optical apertures. The outside finishing matches that of the scanning laser ophthalmoscope to which it is fitted, tightly, in an easily reversible way as a clip-on. The posterior aperture of the device is protected with a high quality plain glass, at least 40 mm long on both sides, 20 mm wide superior and 18 mm wide inferior. The aperture is slanted to eliminate unwanted reflections at an angle of 15.6 degrees γ, and is as such parallel with the window of the scanning laser ophthalmoscope 46 and centered on the optical axis PS. A slide bar or screw 48 for the adjustment of the pupillary distance PD in the range of 28 mm to 35 mm (adult average of 32 mm) is provided on the left and right side of the encasement. Slots 50 are provided at both rectangular anterior apertures, 18 mm by 15 mm, to accommodate different optical filters and lenses. Two additional slots 52 are provided for introducing the filters 54 and lenses 56 in an oblique fashion relative to the optical axis.

MODIFICATION AND EXTENSION OF THE OPTICAL PATHWAYS

With a modification and extension of the scanning laser ophthalmoscope optics it is possible to [1] present part of the same laser beam raster with graphics to one or both eyes, [2] to observe either retina, with or without graphics under real-time conditions on the monitor and [3] to switch between all possibilities without moving the scanning laser ophthalmoscope and subject relative to each other. In general, this is realized by [1] beamsplitting the scanning superimposed infra-red and red laserbeams at the exit aperture of the scanning laser ophthalmoscope. Two optical paths of near identical length span the pupillary distance PD, a value between 28 and 36 mm, on either side and deliver the same laser beam raster with graphics to both eyes in optimal Maxwellian view. [2] The insertion of a combination of bandpass filters for 632.8 nm or 780 nm in the optical paths. [3] Easy switching of these filters between the optical paths. The filters allow monocular or binocular presentation of graphics and observation of either retina during the presentation of graphics or in the absence of graphics on the retina.

A compromise is necessary between the size of the binocular field of view that can be obtained and the maximum possible size of the device. Several constraints are present: physically, because the optical pathlength is increased on both sides by the pupillary distance PD from the midnose to the pupil, the eyes have to come closer to the SLO to neutralize this difference, with additionally the beamsplitting optics in between. Enough space has to remain for such bodily parts as the nose and the eyelashes. As such, the pivot point P of the Maxwellian view will stay in the pupillary plane. Usually, a video frame has a ⅔ aspect ratio that would correspond to monocular angles of view of approximately 23.4 degrees vertically by 32.7 degrees horizontally. A reduced horizontal angle δ of 11.7 degrees and full vertical angle of 23.4 degrees for the binocular field of view has been chosen to satisfy the compromise. This will leave about 16 mm between the anterior edge of the device and the apex of the cornea. The binocular field of view encompasses about 8 optic disc areas and shows enough vascular pattern so that each picture can easily be cut and pasted or referenced to the larger monocular field of view taken without the device. The binocular field of view can be enlarged by a factor of up to 1.6 if a positive lens is inserted in slot 50 on either side and the prefocussing of the laserbeam corrected accordingly.

Certain values used in the engineering drawing of the device are case dependent. These values are the horizontal and vertical angles of the monocular field of view α,β, the slanted angle γ of the scanning laser ophthalmoscope window 46, the reduced horizontal angle of the binocular field of view δ the optical axis represented by the line segment PS, the pupillary distance PD for both eyes. The point D is the intersection of the monocular optical axis with the pupillary planes of both eyes. The point P is the pivot point for the Maxwellian view in both eyes and point S is the intersection between the optical axis and scanning laser ophthalmoscope window 46. The laser raster is assumed to be rectangular although in reality it is slightly trapezoid because of the inherent asymmetry of optics within the scanning laser ophthalmoscope. The angles α and β are measured by projecting the laser raster onto a vertical surface, 666 mm from the pivot point P in air. The mean width of the laser raster at this surface is 375 mm. The height of the laser raster at the vertical surface is 270 mm. The mean horizontal width of the laser raster at the key reference plane 4 is 46.5 mm. The height of the laser raster at the slanted key reference plane 46 is 35.5 mm. From these values the length of the optimal PS line segment in air can be calculated and is 82.6 mm. The actual localization of P can be somewhat variable within each eye. The theoretical external angles of the monocular and binocular field of views are also derived from these values and are respectively α equal to 32.7 degrees β equal to 23.4 degrees. δ equal to 11.7 degrees by choice is one half the value of β and one third of the value of α.

Other important numerical values are the dimensions of the scanning laser ophthalmoscope window or reference plane 46, 95 mm high, 89 mm wide and 10 mm deep. The intersection of the optical axis PS with the key reference plane of the scanning laser ophthalmoscope is located at 43 mm from the inferior edge. The slantness of the reference plane has been measured before as γ equal to 15.6 degrees.

The pivot point of the Maxwellian view illumination P has an optimal position within the pupil of the eye and has to be adjusted in accordance with the PD of both eyes. This adjustment is made by modifying the position of the flat mirrors 58 and 60 with the help of a screw or slide bar 48. The pupillary distance PD is measured beforehand with a pupillometer. If the position of the pivot point P is not optimized, then vignetting will occur. Also the same prefocussed laserbeam is projected on the retina in both eyes and therefore ametropia has to be compensated with the help of external glasses. Small variations in right and left pupillary distance PD and anisometropia are relatively common and have to be taken into account for each eye. Small asymmetries in pupillary distance PD will result in a small difference in axial localization of the pivot P in right and left eye. Anisometropia and PD asymmetry have no influence on the binocular field of view. Common ametropia to both eyes is adjusted with the prefocussing unit of the scanning laser ophthalmoscope. Moving both right and left pivot point P in the same amount along the visual axis by moving the scanning laser ophthalmoscope is possible but limited by the vignetting of the laser raster at the pupil margin. This movement also will not affect focussing in either eye or significantly alter the binocular field of view.

The size of the beamsplitter 62 and flat mirrors 58, 60, 64 is derived from the engineering drawing, some liberty exists in shape and size. They are mounted in such a fashion that the optical path to the beamsplitter and the optical paths from the last mirrors 58, 60 to the pivot point P on either side are co-planar and parallel. Flat mirrors 58, 60, 64 are optimally coated for reflectance of the wavelengths used. This coating depends on the wavelengths, angle of incidence and polarization status of the light. MAXBRIte™ series/003 (Melles-Griot, Irvine, Calif.) are suitable coatings for this purpose. The choice of the dielectric coatings for the beamsplitter 62 depends again on the wavelengths used, their polarization status, and the angle of incidence of the laserlight. Achromatic beamsplitters have a constant transmission/reflection ratio for an extended wavelength range. The ideal beamsplitter is also nearly non-absorbing and as such the reflectance will be independent of the angle of incidence of the laserlight. The beamsplitter 62 consists of a single plane-parallel glassplate with a partially reflecting low absorption dielectric coating on one side. The other side has an antireflection coating optimized for the angle of incidence of 45 degrees. This will prevent ghost images appearing on the video display monitor. A sample coating is HEBBAR™ (Melles-Griot, Irvine, Calif.). Some beamsplitters are highly polarization sensitive.

In a particular scanning laser ophthalmoscope, the infrared laser has vertical polarization of the E vector, p-plane with regard to the beamsplitter 62. The He-Ne laser has horizontal polarization of the E vector, s-plane with regard to the beamsplitter Often ideal transmission-reflection characteristics can not be realized for all wavelengths involved. Because of this difference, an additional neutral density filter 54 and/or polarizer 54 may be necessary on one or both sides to equalize the power of the reflected and transmitted He-Ne red, diode infra-red or argon blue laserbeams. After equalizing, the intensity of the graphics presentation will look similar to both eyes and the retinal image of both eyes will have the same potential brightness on the display monitor, eliminating the need for additional electronic adjustments on the monitor. High quality glass or Fresnel spherical, cylindrical, and prismatic lenses and prisms 56 are used to correct ametropias at the exit aperture slots 50. Fresnel lenses have the additional advantage of being lightweight and thin.

All possibilities of viewing the right or left retina and presenting the graphics to either eye are derived from combining the barrier, edge, and bandpass filters 54 that are described.

The infrared cut-off filter is for example a dichroic interference type filter transmitting 85% of the light at 632.8 nm but blocking 99% of the light at 780 nm. Kodak glass Wratten filter 301A corresponds to these specifications. The filter allows the subject to observe the visible portion of the laser raster with graphics at 632.8 nm without the 780 nm. Therefore no image of the retina will be available on the monitor and the other eye can be observed without the infra-red cut-off filter. This infra-red cut-off filter is essentially a reflector for 780 nm, so called hot mirror, which implies that positioning in the optical pathway is critical to avoid reflection artifacts with oversaturation of the photodetector. Alternative selective absorbers can also be used.

The presence of a 632.8 nm barrier filter determines whether the laser graphics is perceived by the subject or not. Kodak gelatin Wratten filter 89B for example satisfies the specifications. At 780 nm 87% of the light will be transmitted, at 632.8 nm no light will be transmitted at all and no laser raster graphics will be seen by the subject. Filters 54 are inserted in 50 or in the slightly angulated slots 52 if specular reflections are an issue.

Several alternatives exist when selecting bandpass or edge filters for either 632.8 nm and 792 nm. Common absorbers are colored glasses. The Kodak Wratten filter 89 B which is a gelatin filter has been discussed above. It is and edge filter passing 87 % of the light at 792 nm but 0% at 632.8 nm. Other candidates are:Schott Glass type BG1, BG3, FG3 and specifically RG9 Melles-Griot # 03FCG115. KG3 Melles-Griot #03FCG167 does the opposite:70% transmittance at 632.8 nm and less than 5% at 792 nm. Interference type filters or beamsplitters reflect the non-transmitted wavelength and may cause problems with reflections as mentioned before. In this category we have the so called hot and cold mirrors with multilayer dielectric coating, transmittances range between 0 and 85%; the long and short wavelength edge beamsplitters, centered around 700 nm; and the specific bandpass interference filters. Polarization,angle of incidence, and specular reflections may be an issue.

The insertion of optical filters 54, beamsplitter 62, and lenses 56 in the optical pathway reduces the power of the laserlight that illuminates the retina and additionally reduces the amount of light collected by the photodetector for each retina. From each unit of power at the exit aperture of the scanning laser ophthalmoscope on average 50% is diverted by the beam splitter, some is absorbed within the optics or reflected, both in the illumination and return paths. Therefore under binocular illumination conditions a smaller fraction of the light will reach the photodetector when compared with monocular illumination conditions. It is reasonable to use laser sources that are more powerful. These sources are already available in the monocular scanning laser ophthalmoscope for indocyanin green angiography and are easily adapted for use with the binocular instrument by s/he skilled in the art.

The appropriate pair of filters 54 are manually removed and inserted in slots 50 or 52 It is possible to automatize the switching of filters by moving electro-mechanically the different possible combinations. For this purpose a rotating filterwheel can be used in both sides of the optical path.

A pair of liquid crystal shutters 66 can be used in the optical pathways to both eyes to increase the speed of switching between the visualization of both retinas on the display monitor. The synchronization of the filters 68 can be tied to the video display on the monitor. For example each even videofield can represent the left eye and each odd videofield can be made to represent the right eye. Methods to represent both images simultaneously and flicker-free on one or two display monitors, spatially or temporally separated, are well known in the art. A typical twisted nematic liquid-crystal switch consist of a liquid-crystal cell sandwiched between two crossed linear polarizers. The orientation of the polarizers corresponds to the orientation of the polarization of the infra-red laserbeam.

SUMMARY, RAMIFICATIONS, AND SCOPE

The binocular scanning laser ophthalmoscope is an electro-optical device that expands the range of clinical applications of the conventional scanning laser ophthalmoscope.

In imaging, bilateral simultaneous recordings of angiographies are possible. Prism or angular deviations can be precisely measured in small angle diplopia, microstrabismus, and anomalous correspondence. Summation effects of bilateral pattern visual evoked responses can be documented in clinical electrophysiology. Binocular summation activity at the brain level can be investigated for a number of psychophysical tasks including fixation, acuity, reading, and contrast sensitivity.

With the device it is possible to present the same scanning laser raster with or without graphics to one eye only or to both eyes simultaneously. Four combinations are therefore possible. At the same time a set of specific filters in the optical pathway of the invention allows observation of either retina that is covered by the laser raster with or without graphics on the display monitor. The construction enables switching between the different options without moving the scanning laser ophthalmoscope raster and subject relative to each other. Additional lenses can be inserted in the optical pathway for the correction of ametropia. A pupillary distance control for both eyes optimizes the Maxwellian view on the visual axis of both eyes.

Although the description above contains many specificities, these should not be construed as limiting the scope of the invention but as merely providing illustrations of some of the presently preferred embodiments of this invention. Other embodiments of the invention including additions, subtractions, deletions, or modifications of the disclosed embodiment will be obvious to those skilled in the art and are within the scope of the following claims. The scope of the invention should be determined by the appended claims and their legal equivalents, rather than by the examples given.

I claim:

1. A binocular scanning laser ophthalmoscope comprising of:

A. a scanning laser ophthalomoscope using a combination of two different wavelengths, B. electro-optical means for projecting a scanning laser raster with graphics onto both retinas simultaneously, using a combination of beamsplitter and flat mirrors; whereby it becomes unnecessary to move said scanning laser ophthalmoscope from one eye to the other over the pupillary distance in order to project said scanning laser raster with graphics onto either or both said retinas, C. electro-optical means for detecting the return light from eighter retina as desired, usign a combination of optical filters inclduing neutral density filters, polarizing filters, selective wavelength barrier filters, liquid crystal switches, and refractive lenses; whereby observation of either said retina is possible without the need for movign said scanning laser ophthamoscope from one eye to the other over the pupillary distance.

2. The binocular scanning laser ophthalmoscope according to claim 1 further including an electro-mechanical means for rapidly changing said combination of optical filters; whereby graphics can be projected onto one or both said retinas simultaneously and either said retina can be observed on a monitor in whatever combination desired.

3. The binocular scanning laser ophthalmoscope according to claim 1, comprising the improvement of an electronic circuitry for synchronizing the switching of said combination of optical filters, including liquid crystal shutters, to the frequency of the video used in said scanning laser ophthalmoscope.

4. The binocular scanning laser ophthalmoscope according to claim 1 wherein said beamsplitter, said flat mirrors, and said optical filters are optimally coated for the different wavelengths, angle of incidence, and polarization status of used laser sources; hereby optimizing the different possible combinations of graphics projection and observation of said retinas.

5. The binocular scanning laser ophthalmoscope according to claim 1 further comprising the means for adjusting the pupillary distance PD of both eyes; whereby said means will optimize the Maxwellian view in the pupil area of both eyes.

6. A scanning laser ophthalmoscope with electro-optical means for binocular presentation of graphics to both retinas and observation of both said retinas, said electro-optical means including:

A. electro-optical means for generating one scanning laser raster with graphics using two different wavelengths, B. a beamsplitter in combination with flat mirrors to project the same said scanning laser raster with graphics onto either or both said retinas and allowing the observation of said retinas onto a monitor, C. a combination of optical components including neutral density filters, polarizing filters, selective wavelength barrier filters, liquid crystal switches, and refractive lenses whereby it becomes possible to combine as desired the observation of either retina with the projection of graphics onto one or both retinas simultaneously and not having to move the said scanning laser ophthalmoscope from one eye to the other over the pupillary distance for this purpose.

7. The binocular scanning laser ophthalmoscope according to claim 6 further including an electro-mechanical means for rapidly changing said combination of optical components; whereby graphics can be projected onto one or both said retinas simultaneously and either said retina can be observed on a monitor in whatever combination desired.

8. The binocular scanning laser ophthalmoscope according to claim 6, comprising the improvement of an electronic circuitry for synchronizing the switching of said combina tion of optical components, including liquid crystal shutters, to the frequency of the video used in said scanning laser ophthalmoscope.

9. The binocular scanning laser ophthalmoscope according to claim 6 wherein said beamsplitter, said flat mirrors, and said optical components are optimally coated for the different wavelengths, angle of incidence, and polarization status of used laser sources; hereby optimizing the different possible combinations of graphics projection and observation of said retinas.

10. The binocular scanning laser ophthalmoscope according to claim 6 further comprising the means for adjusting the pupillary distance PD of both eyes; whereby said means will optimize the Maxwellian view in the pupil area of both eyes.

* * * * *